US008140165B2

(12) United States Patent
Bühlmann et al.

(10) Patent No.: US 8,140,165 B2
(45) Date of Patent: Mar. 20, 2012

(54) INDEPENDENT PROTECTION SYSTEM FOR AN ELECTRICAL MUSCLE STIMULATION APPARATUS AND METHOD OF USING SAME

(75) Inventors: Félix Bühlmann, Lausanne (CH); Etienne Dunant, Peney-le Jorat (CH); Steve Guex, Prangins (CH); David Truffer, Ecublens (CH); Pierre-Yves Müller, Collonge-Bellerive (CH)

(73) Assignee: Encore Medical Asset Corporation, Henderson, NV (US)

( * ) Notice: Subject to any disclaimer, the term of this patent is extended or adjusted under 35 U.S.C. 154(b) by 845 days.

(21) Appl. No.: 11/343,245

(22) Filed: Jan. 30, 2006

(65) Prior Publication Data

US 2006/0217768 A1    Sep. 28, 2006

Related U.S. Application Data

(60) Provisional application No. 60/648,324, filed on Jan. 28, 2005.

(51) Int. Cl.
*A61N 1/00* (2006.01)
(52) U.S. Cl. ............................................ 607/48
(58) Field of Classification Search ............ 607/48, 607/5
See application file for complete search history.

(56) References Cited

U.S. PATENT DOCUMENTS

| | | | |
|---|---|---|---|
| 2,263,205 A | 11/1941 | Conrad | |
| 3,344,792 A | 10/1967 | Offner at al. | |
| 3,628,538 A | 12/1971 | Vincent et al. | |
| 3,810,457 A | 5/1974 | Bottcher et al. | |
| 3,918,459 A | 11/1975 | Horn | |
| 4,019,518 A | 4/1977 | Maurer et al. | |
| 4,068,669 A | 1/1978 | Niemi | |
| 4,088,141 A | 5/1978 | Niemi | |
| 4,177,819 A | 12/1979 | Kofsky et al. | |
| 4,256,116 A | 3/1981 | Meretsky et al. | |
| 4,324,253 A | 4/1982 | Greene et al. | |
| 4,342,317 A | 8/1982 | Axelgaard | |

(Continued)

FOREIGN PATENT DOCUMENTS

DE    3216911    11/1983

(Continued)

OTHER PUBLICATIONS

"*Cyclotec Pain Control Products*," Cyclotec AMT, 3 pages. Retrieved from http://www.cyclotecamt.com/pages2/products.htm on May 25, 2004.

(Continued)

*Primary Examiner* — Eric D. Bertram
*Assistant Examiner* — Elizabeth K So
(74) *Attorney, Agent, or Firm* — Ropes & Gray LLP

(57) ABSTRACT

Electrotherapy systems and methods for delivering an electrostimulation treatment program to a user while reducing the risk of inducing cardiac fibrillation. The systems and methods detect electrostimulation treatment program delivery characteristics, including a pulse intensity above a preset limit; a pulse duration above a preset limit; an inappropriately compensated pulse; a charge per pulse above a predetermined limit; a current improperly exiting from a stimulation channel; a current present outside of a pulse; an excitation pulse and a compensation pulse generated on different channels; an inter-pulse time less than a predetermined limit; and a time between an excitation and a compensation pulse greater than a predetermined limit. The limits are selected in relation to an objective of reducing the risk of inducing cardiac fibrillation.

24 Claims, 5 Drawing Sheets

U.S. PATENT DOCUMENTS

| | | | |
|---|---|---|---|
| 4,363,324 A | 12/1982 | Kusserow | |
| 4,372,319 A | 2/1983 | Ichinomiya et al. | |
| 4,390,023 A | 6/1983 | Rise | |
| 4,392,496 A | 7/1983 | Stanton | |
| 4,408,609 A | 10/1983 | Axelgaard | |
| 4,503,863 A | 3/1985 | Katims | |
| 4,535,777 A | 8/1985 | Castel | |
| 4,569,352 A | 2/1986 | Petrofsky et al. | |
| 4,582,063 A | 4/1986 | Mickeiwicz et al. | |
| 4,586,495 A | 5/1986 | Petrofsky | |
| 4,614,178 A | 9/1986 | Harlt et al. | |
| 4,632,117 A | 12/1986 | James | |
| 4,640,286 A | 2/1987 | Thomson | |
| 4,664,118 A | 5/1987 | Batters | |
| 4,669,477 A | 6/1987 | Ober | |
| 4,706,674 A | 11/1987 | Dieken et al. | |
| 4,769,881 A | 9/1988 | Pedigo et al. | |
| 4,785,813 A | 11/1988 | Petrofsky | |
| 4,803,988 A | 2/1989 | Thomson | |
| 4,805,636 A | 2/1989 | Barry et al. | |
| 4,811,742 A | 3/1989 | Hassel et al. | |
| 4,848,347 A | 7/1989 | Hall | |
| 4,887,603 A | 12/1989 | Morawetz et al. | |
| 4,919,139 A | 4/1990 | Brodard | |
| 4,926,865 A | 5/1990 | Oman | |
| 4,976,264 A | 12/1990 | Petrofsky | |
| 4,977,895 A | 12/1990 | Tannenbaum | |
| 4,996,987 A | 3/1991 | Petrofsky | |
| 5,041,974 A | 8/1991 | Walker et al. | |
| 5,048,522 A | 9/1991 | Petrofsky | |
| 5,067,495 A | 11/1991 | Brehm | |
| 5,070,873 A | 12/1991 | Graupe et al. | |
| 5,081,989 A | 1/1992 | Graupe et al. | |
| 5,092,329 A | 3/1992 | Graupe et al. | |
| 5,113,176 A | 5/1992 | Harris | |
| 5,117,826 A | 6/1992 | Bartelt et al. | |
| 5,123,413 A | 6/1992 | Hasegawa et al. | |
| 5,131,401 A | 7/1992 | Westenskow et al. | |
| 5,161,530 A | 11/1992 | Gamble | |
| 5,178,156 A | 1/1993 | Takishima et al. | |
| 5,184,617 A | 2/1993 | Harris et al. | |
| 5,233,987 A | 8/1993 | Fabian et al. | |
| 5,285,781 A | 2/1994 | Brodard | |
| 5,300,096 A | 4/1994 | Hall et al. | |
| 5,350,414 A | 9/1994 | Kolen | |
| 5,397,338 A | 3/1995 | Grey et al. | |
| 5,413,550 A | 5/1995 | Castel | |
| 5,507,788 A | 4/1996 | Lieber | |
| 5,512,057 A | 4/1996 | Reiss et al. | |
| 5,514,165 A | 5/1996 | Malaugh et al. | |
| 5,540,235 A | 7/1996 | Wilson | |
| 5,540,735 A | 7/1996 | Wingrove | |
| 5,562,718 A | 10/1996 | Palermo | |
| 5,653,739 A | 8/1997 | Maurer et al. | |
| 5,732,401 A | 3/1998 | Conway | |
| 5,748,845 A | 5/1998 | Labun et al. | |
| 5,755,745 A | 5/1998 | McGraw et al. | |
| 5,775,331 A | 7/1998 | Raymond et al. | |
| 5,776,171 A | 7/1998 | Peckham et al. | |
| 5,776,173 A | 7/1998 | Madsen, Jr. et al. | |
| 5,782,893 A | 7/1998 | Dennis, III | |
| 5,800,458 A | 9/1998 | Wingrove | |
| 5,817,138 A | 10/1998 | Suzuki | |
| 5,836,995 A | 11/1998 | MGraw et al. | |
| RE35,987 E | 12/1998 | Harris et al. | |
| 5,873,900 A | 2/1999 | Maurer et al. | |
| 5,954,758 A | 9/1999 | Peckham et al. | |
| 5,961,542 A | 10/1999 | Agarwala | |
| 5,967,975 A | 10/1999 | Ridgeway | |
| 5,980,435 A | 11/1999 | Joutras et al. | |
| 6,026,328 A | 2/2000 | Peckham et al. | |
| 6,029,090 A | 2/2000 | Herbst | |
| 6,041,259 A | 3/2000 | Agarwala et al. | |
| 6,044,303 A | 3/2000 | Agarwala et al. | |
| RE36,690 E | 5/2000 | McGraw et al. | |
| 6,064,911 A | 5/2000 | Wingrove | |
| 6,086,525 A | 7/2000 | Davey et al. | |
| 6,113,552 A | 9/2000 | Shimazu et al. | |
| 6,146,335 A | 11/2000 | Gozani | |
| 6,233,472 B1 | 5/2001 | Bennett et al. | |
| 6,285,906 B1* | 9/2001 | Ben-Haim et al. | 607/4 |
| 6,292,692 B1 | 9/2001 | Skelton et al. | |
| 6,324,432 B1 | 11/2001 | Rigaux et al. | |
| 6,393,328 B1 | 5/2002 | McGraw et al. | |
| 6,432,074 B1 | 8/2002 | Ager et al. | |
| 6,445,955 B1 | 9/2002 | Michelson et al. | |
| 6,560,487 B1 | 5/2003 | McGraw et al. | |
| 6,564,103 B2 | 5/2003 | Fischer et al. | |
| 6,584,358 B2 | 6/2003 | Carter et al. | |
| 6,609,031 B1 | 8/2003 | Law et al. | |
| 6,612,984 B1 | 9/2003 | Kerr, II | |
| 6,628,492 B2 | 9/2003 | Akiyama et al. | |
| 6,647,290 B2* | 11/2003 | Wuthrich | 607/5 |
| 6,662,051 B1 | 12/2003 | Eraker et al. | |
| 6,675,048 B2 | 1/2004 | McGraw et al. | |
| 6,684,106 B2 | 1/2004 | Herbst | |
| 6,701,189 B2 | 3/2004 | Fang et al. | |
| 6,727,814 B2 | 4/2004 | Saltzstein et al. | |
| 6,826,429 B2 | 11/2004 | Johnson et al. | |
| 6,839,594 B2 | 1/2005 | Cohen et al. | |
| 6,845,271 B2 | 1/2005 | Fang et al. | |
| 6,876,883 B2 | 4/2005 | Hurtado | |
| 6,907,295 B2 | 6/2005 | Gross et al. | |
| 6,963,773 B2* | 11/2005 | Waltman et al. | 607/5 |
| 6,988,005 B2 | 1/2006 | McGraw et al. | |
| 2001/0051787 A1 | 12/2001 | Haller et al. | |
| 2002/0165590 A1 | 11/2002 | Crowe et al. | |
| 2003/0036683 A1 | 2/2003 | Kehr et al. | |
| 2003/0074037 A1 | 4/2003 | Moore et al. | |
| 2004/0010291 A1* | 1/2004 | Wagner et al. | 607/5 |
| 2004/0147975 A1 | 7/2004 | Popovic et al. | |
| 2004/0167585 A1 | 8/2004 | Kovak et al. | |

FOREIGN PATENT DOCUMENTS

| | | |
|---|---|---|
| DE | 4029175 | 3/1992 |
| EP | 0269844 A1 | 6/1988 |
| EP | 0367338 | 8/1993 |
| EP | 0706806 | 4/1996 |
| FR | 2425865 A1 | 12/1979 |
| FR | 2504807 A1 | 11/1982 |
| JP | 2004081676 | 3/2004 |
| WO | WO82/00414 | 2/1982 |
| WO | WO8602567 A1 | 5/1986 |
| WO | WO9510323 A1 | 4/1995 |
| WO | WO9919019 A1 | 4/1999 |
| WO | WO-9941682 | 8/1999 |
| WO | WO00/01055 | 1/2000 |
| WO | WO-0036900 | 6/2000 |
| WO | WO-0103768 | 1/2001 |
| WO | WO 02085452 | 10/2002 |
| WO | WO-03008038 | 1/2003 |
| WO | WO-2004011087 | 2/2004 |
| WO | WO-2004012807 | 2/2004 |
| WO | WO-2004018038 | 3/2004 |
| WO | WO-2004064915 | 8/2004 |

OTHER PUBLICATIONS

"*Muscle Stimulator and TENS: Very different modalities,*" RS Medical, 1 page. Retrieved from http://www.rsmedical.com/products/diff/body.htm on Apr. 27, 2004.

"*Netwave,*" Blue Sky Labs; 6 pages; Copyright 2003.

"*RS-4i Sequential Stimulator,*" 6 pages; Retrieved from http://www.rsmedical.com/products/rs2/body.htm on Apr. 27, 2004.

"*501 (k) Summary for netwave Interferential Stimulator,*" Ryan Telemedicine, LLC; Jun. 12, 2003.

Ilic et al., "*A Programmable Electronic Stimulator for FES Systems,*" IEE Transactions on Rehabilitation Engineering, vol. 2, No. 4, Dec. 1994.

* cited by examiner

INDEPENDENT PROTECTION SYSTEM FOR AN ELECTRICAL MUSCLE STIMULATION APPARATUS AND METHOD OF USING SAME

RELATED APPLICATION

The present application claims priority to U.S. Provisional Patent Application Ser. No. 60/648,324, filed Jan. 28, 2005, and entitled "INDEPENDENT PROTECTION SYSTEM FOR AN ELECTRICAL MUSCLE STIMULATION APPARATUS AND METHOD OF USING SAME," which is incorporated herein by reference in its entirety.

FIELD OF THE INVENTION

The invention relates generally to electrostimulation. More particularly, the invention is directed to an apparatus and method for electrical muscle stimulation wherein the apparatus includes an independent protection system that supervises generated stimulation pulses to reduce the risk of inducing cardiac fibrillation.

BACKGROUND OF THE INVENTION

It is common practice for therapists, physicians, athletes, and other individuals to utilize various electrostimulation treatment and therapy devices to promote muscle training, conditioning, and growth. In addition, devices often referred to as Transcutaneous Nerve Stimulation ("TENS") units are employed to manage pain and discomfort by blocking the nerve signals from the area of discomfort to the brain. With muscle stimulation and nerve stimulation, a device is programmed to output various levels of electrical pulses. The frequency, duration, pulse width, and intensity of the output signal control the directed treatment goals.

With regard to muscle stimulation, there are a myriad of uses for these electrostimulation devices. Treatment categories can generally be divided between fitness, aesthetic, sport, pain management, rehabilitation, and vascular. Each is directed to a different stimulation goal. With fitness, the goal is generally to restore, improve, or maintain a good physical condition by building muscle, muscle tone, volume, trophism, metabolism, and the like. With aesthetic goals, the stimulator is often utilized on muscles in order to shape, firm, increase elasticity, refine, and increase caloric expenditure. Sports-minded individuals may use the device to increase muscular endurance and strength, increase blood flow to promote active recovery, and the like. When focus is on rehabilitation, muscular stimulation is needed to restore or otherwise redevelop a convalescent muscle. Under the vascular category of treatment programs, the goal is to improve blood circulation in the stimulated area to minimize circulatory problems, fatigue, lack of oxygenation, swelling, and other related problems. In pain management applications, electrostimulation devices are used primarily to alleviate muscle pain or other discomfort.

Regardless of the unique goal-dependent outputs of the device, electrostimulation works under a principle of muscle contraction. When an individual voluntarily contracts a muscle, the brain sends the information to the muscle via the motor nerve. With electrostimulation, a suitable electric current acts directly on the nerve by means of electrical impulses that reproduce the natural physiological phenomenon. These electrical impulses are applied to the user through attached electrodes. The electrodes are typically adhesively attached to the person or person's clothing. With electrostimulation a patient or user can achieve intensive muscular work without mental or cardiac fatigue, thus reducing joint and tendon constraints.

While electrostimulation can be used for the above-described purposes, the U.S. Food & Drug Administration (FDA) currently limits or proscribes the use of electrostimulation devices on certain areas of the body, including the pectoralis major (frontal chest/shoulder area) and latissimus dorsi (upper back area) muscle groups, because of the risk of inducing cardiac fibrillation in the event of device malfunction, misuse, or failure. Conventional electrostimulation devices are not capable of providing a level of self-monitoring and protection to permit the safe use of such devices in the cardiac region.

For example, U.S. Pat. No. 4,088,141 to Niemi discloses a fault circuit for a stimulator. The circuit may be incorporated into a medical transcutaneous nerve or muscle stimulator for disabling the output from the stimulator to stimulation electrodes connected thereto upon the occurrence of an undesirable output event of the kind that may result in an electrical shock or burn to a user of the stimulator. See also U.S. Pat. No. 4,068,669 to Niemi.

In U.S. Pat. No. 4,363,324 to Kusserow, a current stimulation apparatus includes a safety circuit. A safety circuit that disconnects the patient output from the operating voltage is employed as the protection installation and also responds when the patient current deviates from a pre-selected desired value adjusted on an intensity adjustment member.

U.S. Pat. No. 4,582,063 to Mickiewicz discloses a transcutaneous nerve stimulation device with sentinel. The device produces a sentinel pulse of known characteristics and an output response is measured. A sentinel warning signal is produced if an undesired output response is measured to alert the user to a potentially hazardous condition.

U.S. Pat. No. 4,706,674 to Dieken discloses an electrical stimulator utilizing an output current monitor. One embodiment of Dieken includes an additional current monitor, wherein a comparator is used to compare currents measured by both current monitors.

EP0367338 to Beun discloses an electrotherapy apparatus. EP0367338 discusses monitoring a sum of two currents to prevent a total output current exceeding a predetermined limit value.

U.S. Pat. No. 5,800,458 to Wingrove, commonly assigned with the present application, is directed to a compliance monitor for monitoring applied electrical stimulation. The compliance monitor comprises a current sensing element, a controller, and a timer. When the current sensing element senses that current is supplied through an output channel, the current sensing element outputs a signal to the controller.

Other documents that generally disclose and discuss various safety and protection schemes and the general state of the art include U.S. Pat. No. 4,769,881 to Pedigo et al., U.S. Pat. Nos. 5,081,989 and 5,092,329 to Graupe et al., U.S. Pat. No. 6,564,103 to Fischer et al., EP 0706806 to Cywinski, WO 82/00414 to Heath, PCT/US81/01055, DE 4029175, and DE 3216911.

While these safety systems can be effective in generally preventing delivery of excessive stimulation pulses, the systems are not specifically designed to prevent delivery of stimulation pulses that could induce cardiac fibrillation. Further, the current systems are not designed for the robust level of safety required to overcome the existing FDA proscription of use of electrostimulation devices on regions of the body where stimulation pulses might inadvertently induce cardiac fibrillation.

The need therefore remains for an electrostimulation device having a protection system that monitors and supervises treatment sessions, providing an elevated level of safety for users.

SUMMARY OF THE DISCLOSURE

The invention solves many of the above described deficiencies and drawbacks inherent with conventional electrostimulation devices and treatments. In particular, various embodiments of the invention are directed to an electrotherapy system including an independent protection system for monitoring at least one characteristic of generated and delivered electrostimulation pulses relevant to preventing inadvertent induction of cardiac fibrillation, and a method of using an electrotherapy system that includes such an independent protection system.

According to one embodiment of the invention, an electrotherapy system for delivering an electrostimulation treatment program to a user with a reduced risk of inducing cardiac fibrillation comprises an electrical pulse generator, at least one electrode assembly, a command module, and an independent protection system. The electrical pulse generator is operable to generate electrical pulses according to an electrostimulation treatment program. The at least one electrode assembly electrically is coupled to the pulse generator by at least one stimulation channel. The command module is coupled to the at least one stimulation channel and is communicatively coupled to the pulse generator to operably control delivery of the electrostimulation treatment program to a user via the electrode assembly. The independent protection system is communicatively coupled to the at least one stimulation channel and the command module and is operable to monitor the electrostimulation treatment program to detect at least one characteristic of the electrostimulation treatment program. The independent protection system is further operable to maintain or alter an operating state of the electrotherapy system based upon the at least one characteristic detected to reduce the risk of inducing fibrillation when the electrotherapy system is applied to muscle groups proximate the cardiac region.

In use, a method of using an electrotherapy system including a safety system to reduce the risk of inducing cardiac fibrillation according to one embodiment of the invention includes applying at least one electrode of an electrotherapy system to a user. An electrostimulation treatment program of the electrotherapy system is selected, and electrostimulation pulses are generated according to the selected program. The pulses are delivered to the user via the at least one electrode. At least one characteristic of the generated and delivered pulses is detected by the safety system, and an operating state of the electrotherapy system is maintained or altered based upon the at least one characteristic detected to reduce the risk of inducing fibrillation when the electrotherapy system is applied to muscle groups proximate the cardiac region.

According to either the systems or methods of the present invention, the at least one characteristic includes a pulse intensity above a preset limit; a pulse duration above a preset limit; an inappropriately compensated pulse; a charge per pulse above a predetermined limit; a current improperly exiting from a stimulation channel; a current present in more than one half-bridge at a time, within a pulse; a current present outside of a pulse; excitation and compensation pulses generated on different channels; a new pulse generated too soon, in effect checking an inter-pulse time according to a predetermined limit; and a time between excitation and compensation pulses too long according to a predetermined limit. The characteristics preferably have limits selected in relation to the objective of reducing the risk of inducing cardiac fibrillation.

The above summary of the invention is not intended to describe each illustrated embodiment or every implementation of the present invention. The figures and the detailed description that follow more particularly exemplify these embodiments.

BRIEF DESCRIPTION OF THE DRAWINGS

The invention may be more completely understood in consideration of the following detailed description of various embodiments of the invention in connection with the accompanying drawings, in which.

Figure 1:
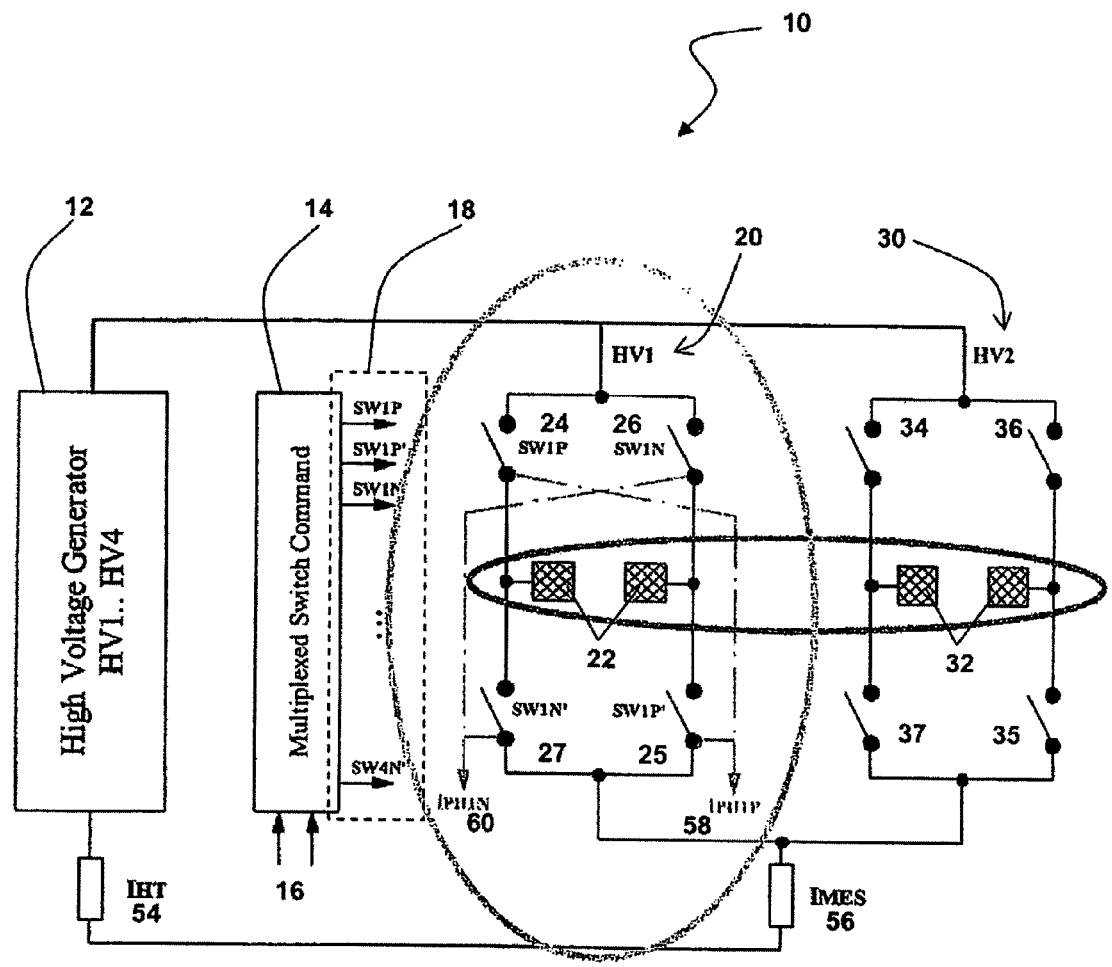
FIG. 1 is a circuit diagram according to one embodiment of the invention.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION OF THE INVENTION

The independent protection system and method of the invention provide an elevated level of monitoring of an electrostimulation system output, permitting application and treatment by patient users and reducing the risk of inducing cardiac fibrillation. The invention can be more readily understood by reference to FIGS. 1-5 and the following description. While the invention is not necessarily limited to such an application, the invention will be better appreciated using a discussion of exemplary embodiments in specific contexts.

Referring to FIG. 1, a system circuit 10 according to one embodiment of the invention is depicted. System circuit 10 is representative of an electrotherapy system operable to provide therapeutic, rehabilitative, or other electrostimulation treatment programs to a user. In one embodiment, system 10 includes a voltage, or pulse, generator 12 electrically coupled to at least one set of electrodes via a stimulation channel. System 10 includes two stimulation channels 20 and 30, each including a set of electrodes 22 and 32, in the embodiment depicted in FIG. 1. In another embodiment, system 10 includes four or more stimulation channels. Each set of electrodes 22 and 32 preferably comprises two patch electrodes adapted to deliver transcutaneous electrical stimulation pulses to a user, although other electrode sets and configurations can be used in other preferred embodiments as appropriate for the particular electrostimulation device or treatment used, or as selected or prescribed by a medical professional.

Stimulation channels 20 and 30 and electrodes 22 and 32 are arranged as H-bridges, with a multiplexed switch command module 14 electrically coupled to switches on each channel 20 and 30. In one embodiment, channel 20 includes four switches, two switches 24 and 25 on a positive branch of the output and two switches 26 and 27 on a negative branch of the output. Channel 30 similarly includes four switches 34-37. Each switch 24-27 and 34-37 is controlled by switch command module 14, which includes an output channel to communicatively interface with each switch. Switch command module 14 includes inputs 16, microprocessor command signals for selecting a half H-bridge, and sixteen output channels 18 in an embodiment in which system 10 includes four stimulation channels.

Switch command module 14 is operable to control switches 24-27 and 34-37 to deliver an electrostimulation treatment program. System 10 can be pre-programmed with one or more treatment programs, or custom programs can be created as needed, depending upon the particular electrostimulation device within which system 10 operates. Electrodes 22 and 32 deliver electrical stimulation pulses according to the program and switch command module 14 selectively activates and deactivates electrodes 22 and 32 by controlling switches 24-27.

Relevant signals and logic states in system 10 are monitored by the independent protection system of the invention to provide an elevated level of patient safety during use. Referring to both FIGS. 1 and 2, a protection system microprocessor 50 is communicatively coupled with system 10 in order to receive electrical signals and logic states as inputs. A timing signal EN 52 is a first input to microprocessor 50. Signal IMES 56 represents the current in each of the channels 20 and 30. This current is the current flowing through the body of a user during treatment. A dI signal 66 detects current leakage, monitoring for a short circuit. Signal IPH1P 58 monitors the positive half of each H-bridge configured stimulation channel 20 and 30. Signal IPH1N 60 similarly monitors the negative half of each H-bridge configured stimulation channel 20 and 30.

Figure 2:
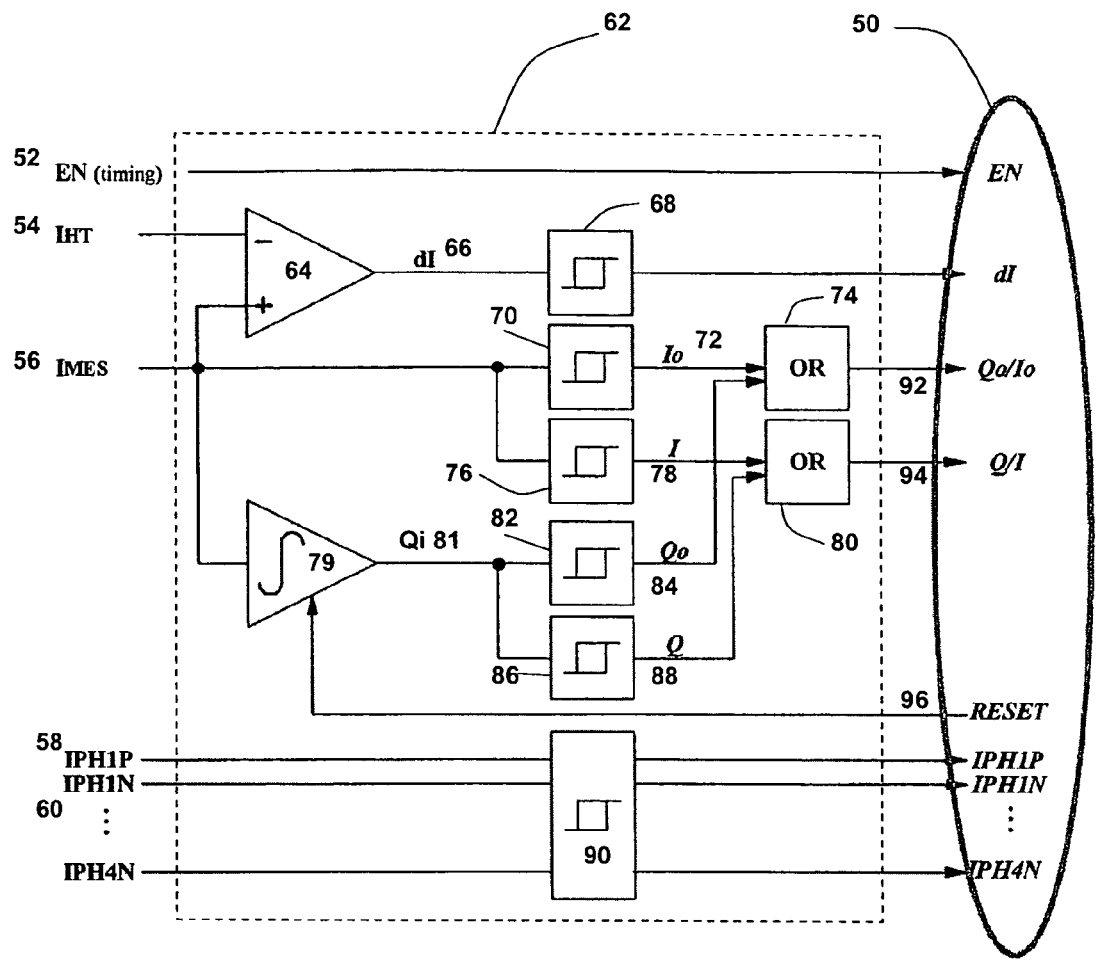
FIG. 2 is another circuit diagram according to one embodiment of the invention.

Signals 54-60 are processed by logic circuit 62 before being input to microprocessor 50 in one embodiment as depicted in FIG. 2. A difference element 64 produces signal dI 66 from input signals IHT 54 and IMES 56. Signal IHT represents a current from high voltage generator 12. Signal dI 66 is then fed through a trigger element 68 to microprocessor 50. Signal IMES 56 is also fed through two triggers 70 and 76 to produce signals Io 72 and I 78, respectively, and through an integrator element 79 to produce signal Qi 81. Signal Qi 81 is subsequently fed through triggers 82 and 86 to produce signals Qo 84 and Q 88.

Signal Io 72 represents a maximum current limit in a state of system 10 in which a stimulation pulse is not generated by generator 12. Signal I 78 represents a maximum current limit in a state of system 10 in which a stimulation pulse is generated by generator 12. Signal Qo 84 is a maximum residual charge limit after a stimulation pulse has been generated, and signal Q is a maximum instantaneous charge during a stimulation pulse.

In one embodiment, trigger elements 68, 70, 76, 82, and 86, and trigger element 90 discussed in more detail below, are window comparators. A window comparator output indicates whether a measured signal is within a voltage bounded by two thresholds, an upper threshold and a lower threshold. Trigger elements 68, 70, 76, 82, 86, and 90 thus trigger if the input signal is outside of the window bounded by the upper and lower thresholds.

Logic circuit 62 next supplies signals Io 72 and Qo 84 to OR gate element 74. Logic signal Qo/Io 92 is input to microprocessor 50. Signals I 78 and Q 88 are fed through OR gate element 80, and logic signal Q/I 94 is input to microprocessor 50. Signals IPH1P 58 and IPH1N 60 are also input to microprocessor 50 as logic signals via trigger element 90. Microprocessor 50 also includes a reset signal 96 electrically connected to integrator element 79.

From the logic signals provided by logic circuit 62, microprocessor 50 supervises system 10, in particular the stimulation pulses generated and delivered to a user to detect, for example, (1) a pulse intensity, I, above a predetermined limit; (2) a pulse duration, T, above a predetermined limit; (3) a pulse inappropriately compensated; (4) a charge, Q, per pulse above a predetermined limit; (5) a current supplied to a user via a first stimulation channel exiting via a second channel; (6) a current present in more than one half-bridge at a time, within a pulse; (7) a current present outside of a pulse; (8) excitation and compensation pulses generated on different channels; (9) a new pulse generated too soon, in effect checking an inter-pulse time according to a predetermined limit; and (10) a time between excitation and compensation pulses too long, according to a predetermined limit. If any of (1)-(10) is detected, microprocessor 50 is operable to shut down system 10.

In one preferred embodiment, the predetermined limit of the pulse intensity, I, is about 152 milliamps (mA); the predetermined limit of the pulse duration, T, is about 1.5 milliseconds (ms); the predetermined limit of the charge per pulse, Q, is about 10 micro-Coulombs ($\mu$C); the predetermined inter-pulse time limit is about 700 microseconds ($\mu$s); and the predetermined time limit between excitation and compensation pulses is about one microsecond ($\mu$s). These predetermined limits may vary, in whole or in part, in other embodiments of the present invention. In one embodiment, the predetermined limits are programmable and adjustable by a medical professional user in relation to patient-specific parameters that could affect the likelihood of an electrical stimulation pulse inadvertently inducing fibrillation if delivered in the pectoral or similar regions of the patient's body.

With respect to characteristics (1)-(10) above, the pulse intensity (I), pulse duration (T), and charge (Q) are related as follows:

$$Q = I * T \qquad \text{Equation 1}$$

$$Q(t) = \int_0^t i(t')dt' \text{ with}(Q(0) = 0) \qquad \text{Equation 2}$$

In one embodiment of system 10, a positive pulse, Q+, must be followed by a negative compensation pulse, Q−, such that the total remaining charge, Q, equals zero and there is no DC offset:

$$Q=(Q+)+(Q-)=0 \qquad \text{Equation 3}$$

In (3) above, microprocessor 50 determines whether a pulse is inappropriately compensated according to Equation 2. In (4), the charge per pulse can be a positive pulse, Q+, or a compensation pulse, Q−.

Figure 3:
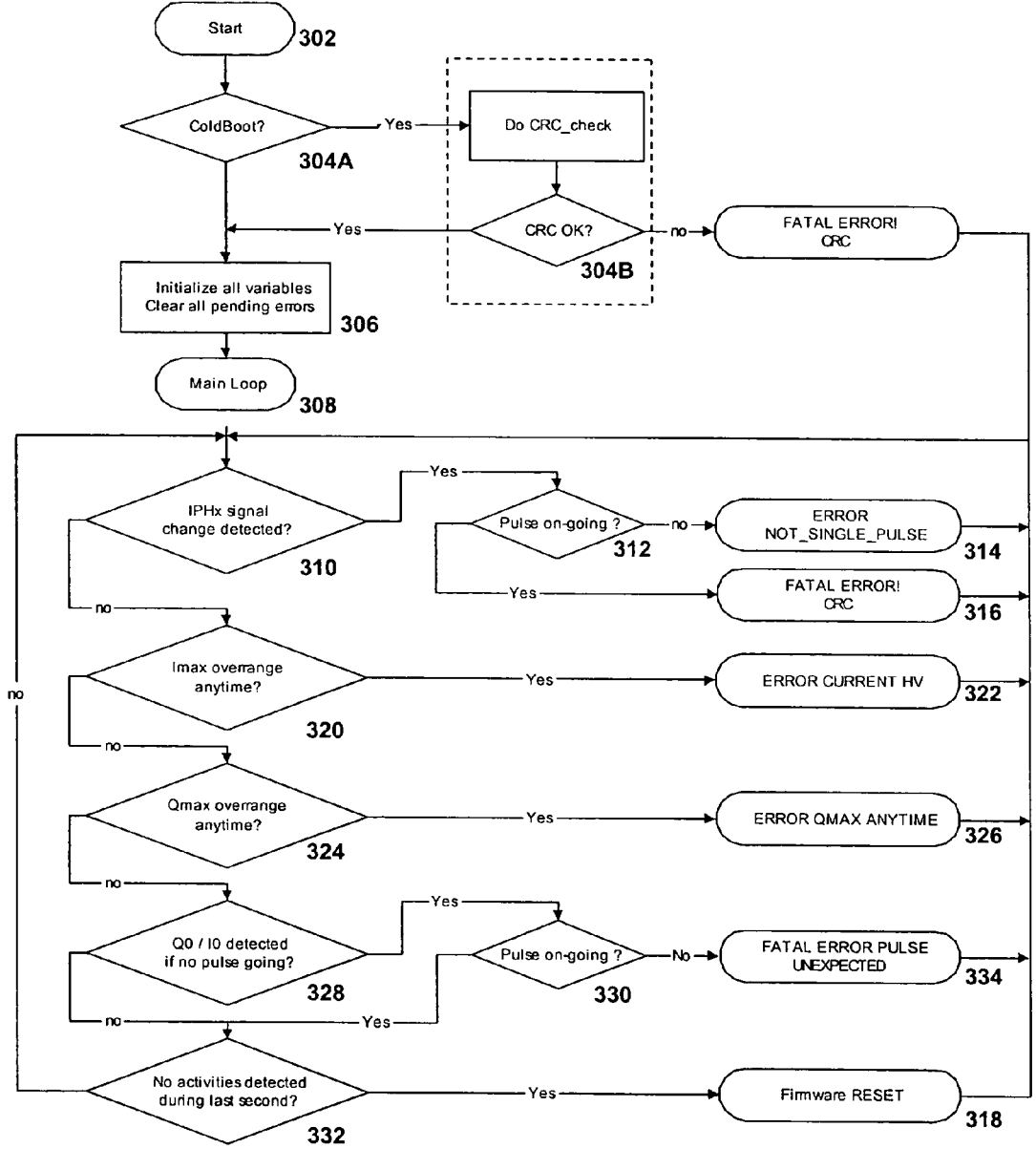
FIG. 3 is a flowchart of a microprocessor main loop according to one embodiment of the invention.

FIG. 3 is a flowchart of one embodiment of a main loop operation 300 of microprocessor 50. At step 302, microprocessor 50 is started. The start-up may be initiated by powering on the electrotherapy device at step 304A, in which case microprocessor 50 performs subroutine 304B. At step 306, microprocessor 50 is initialized prior to entering main loop 308.

In main loop 308, microprocessor 50 evaluates whether a change in signals 58-60, monitoring the H-bridge, has occurred at step 310. If a change has occurred, microprocessor 50 evaluates whether a pulse is on-going at step 312. Whether a pulse is (step 316) or is not (step 314) ongoing, microprocessor 50 reports an error. A firmware reset is initiated at step 318, which must be done to reinitiate the system and cancel the fault mode.

Microprocessor 50 evaluates whether a current signal, Imax or Q/I 94 in FIG. 2, exceeds a limit at step 320. If the limit is exceeded, an error is triggered at step 322 and a firmware reset is initiated at step 318.

A charge signal, Qmax or Q/I 94 in FIG. 2, is evaluated by microprocessor 50 at step 324. If a limit is exceeded, an error is triggered at step 326 and a firmware reset is initiated at step 318.

Signal 92 (refer to FIG. 2 and the description above) is evaluated by microprocessor 50 at step 328. If signal 92 is detected when no pulse is generated, microprocessor 50 evaluates whether a pulse is on-going at step 330. If a pulse is on-going at step 330, or if no signal 92 is detected at step 328, microprocessor 50 evaluates whether any activity was detected within the past second at step 332. A time period longer or shorter than one second may be used in other embodiments of the invention. If activity was detected within the past second, microprocessor 50 returns to the start of main loop 308. If no pulse was on-going at step 330, microprocessor 50 reports an error at step 334 and triggers a firmware reset at step 318. If no activity was detected at step 332, microprocessor 50 initiates a firmware reset at step 318.

Figure 4:
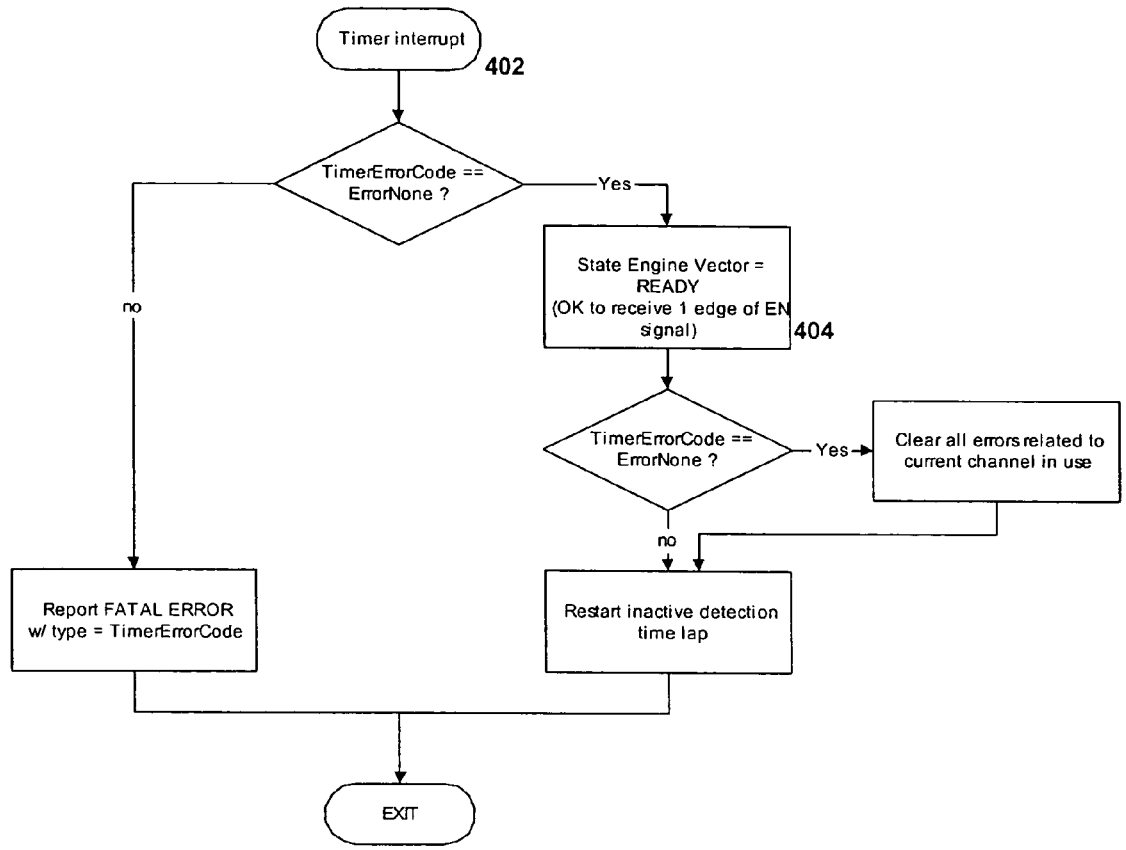
FIG. 4 is a flowchart of interrupts according to one embodiment of the invention.
Figure 4:
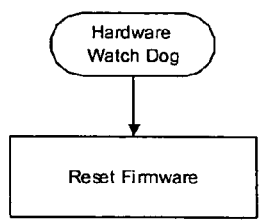
Figure 5:
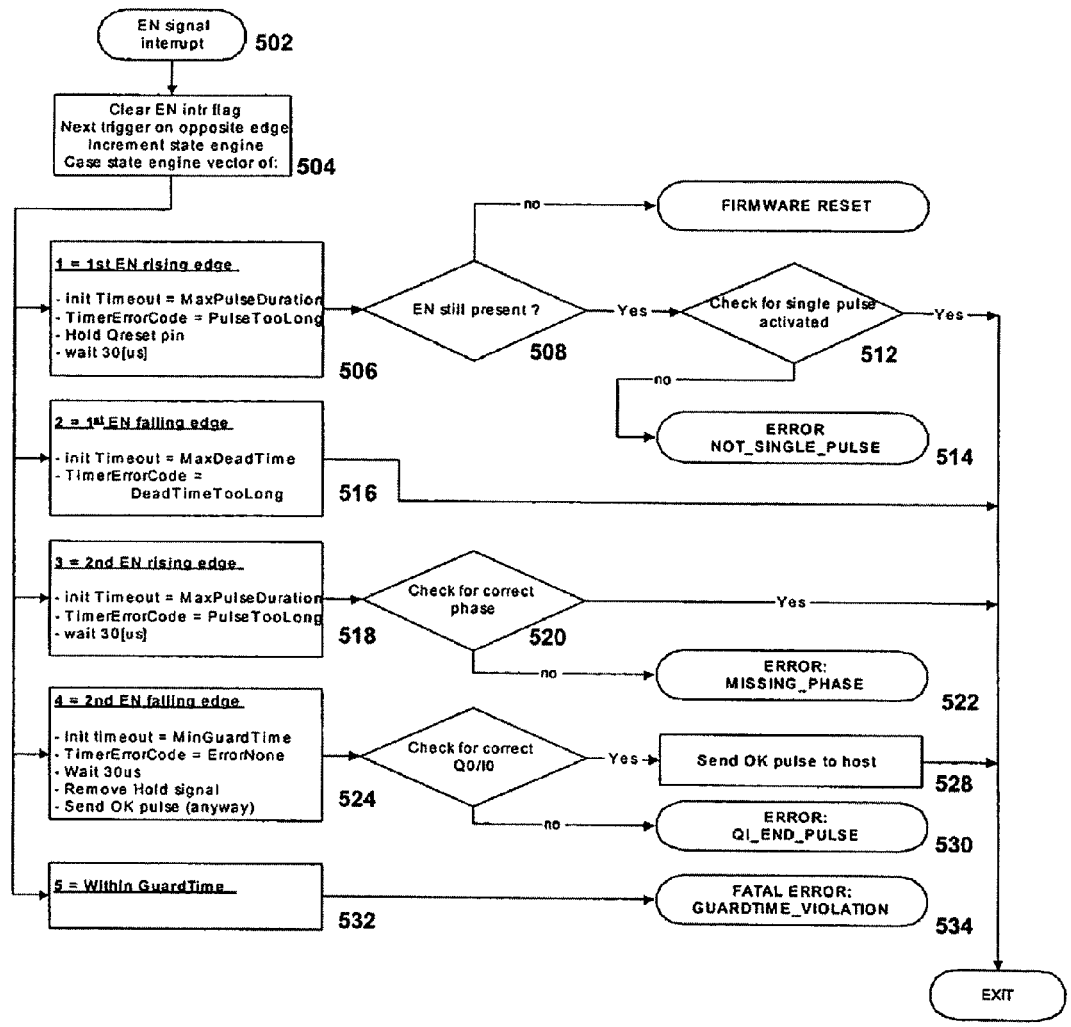
FIG. 5 is a flowchart of interrupt handling according to one embodiment of the invention.

FIG. 4 is a flowchart of interrupts and FIG. 5 is a flowchart of interrupt handling, according to one embodiment of the invention. In timer interrupt 402, at step 404 the state engine vector is ready to receive the first edge of timing signal EN 52 (refer to FIG. 2). In interrupt 502, microprocessor 50 clears the interrupt flag and increments the state engine at step 504. If the state engine vector is 1, microprocessor 50 proceeds to step 506 and evaluates whether signal EN 52 is still present at step 508. If signal EN 52 is present, microprocessor 50 checks for a single pulse at step 512 and either exits interrupt 502 if yes or reports an error at step 514. Step 516 represents a state engine vector of 2. Step 518 represents a state engine vector of 3, and microprocessor 50 checks for a correct phase at step 520. If the phase is correct, microprocessor 50 exits interrupt routine 502. If not, microprocessor 50 triggers an incorrect phase error at step 522. Following step 524, wherein the state machine vector is 4, microprocessor 50 checks for a correct ratio of Qo/Io (signal 92 in FIG. 2). If the ratio is correct, microprocessor 50 proceeds to step 528 and then exits interrupt routine 502. If not, microprocessor 50 reports an error at step 530. At step 532, a state engine vector of 5, microprocessor 50 proceeds to a guardtime violation fatal error at step 534.

One embodiment of an electrotherapy system for delivering an electrostimulation treatment program to a user with a reduced risk of inducing cardiac fibrillation comprises an electrical pulse generator, at least one electrode assembly, a command module, and an independent protection system. The electrical pulse generator is operable to generate electrical pulses according to an electrostimulation treatment program. The at least one electrode assembly electrically is coupled to the pulse generator by at least one stimulation channel. The command module is coupled to the at least one stimulation channel and is communicatively coupled to the pulse generator to operably control delivery of the electrostimulation treatment program to a user via the electrode assembly. The independent protection system is communicatively coupled to the at least one stimulation channel and the command module and is operable to monitor the electrostimulation treatment program to detect at least one characteristic of the electrostimulation treatment program. The independent protection system is further operable to maintain or alter an operating state of the electrotherapy system based upon the at least one characteristic detected to reduce the risk of inducing fibrillation when the electrotherapy system is applied to muscle groups proximate the cardiac region.

In use, a method of using an electrotherapy system including a safety system to reduce the risk of inducing cardiac fibrillation includes applying at least one electrode of an electrotherapy system to a user. An electrostimulation treatment program of the electrotherapy system is selected, and electrostimulation pulses are generated according to the selected program. The pulses are delivered to the user via the at least one electrode. At least one characteristic of the generated and delivered pulses is detected by the safety system, and an operating state of the electrotherapy system is maintained or altered based upon the at least one characteristic detected to reduce the risk of inducing fibrillation when the electrotherapy system is applied to muscle groups proximate the cardiac region.

The at least one characteristic according to the system or method includes a pulse intensity above a preset limit; a pulse duration above a preset limit; an inappropriately compensated pulse; a charge per pulse above a predetermined limit; a current improperly exiting from a stimulation channel; a current present in more than one half-bridge at a time, within a pulse; a current present outside of a pulse; excitation and compensation pulses generated on different channels; a new pulse generated too soon, in effect checking an inter-pulse time according to a predetermined limit; and a time between excitation and compensation pulses too long according to a predetermined limit, all of which have limits selected in relation to the objective of reducing the risk of inducing cardiac fibrillation.

The systems and methods of the present invention as described herein provide a number of advantages. In particular, the independent protection system reduces the flow of DC current. This, in turn, reduces the risk to users of DC burn, an electrochemical burn resulting from DC current flowing through the body and causing local pH changes under the electrodes due to electrolysis taking place.

Although specific embodiments have been illustrated and described herein for purposes of description of an example embodiment, it will be appreciated by those of ordinary skill in the art that a wide variety of alternate and/or equivalent implementations calculated to achieve the same purposes may be substituted for the specific embodiments shown and described without departing from the scope of the present invention. Those skilled in the art will readily appreciate that the invention may be implemented in a very wide variety of embodiments. This application is intended to cover any adaptations or variations of the various embodiments discussed herein, including the disclosure information in the attached appendices. Therefore, it is manifestly intended that this invention be limited only by the claims and the equivalents thereof.

The invention claimed is:

1. An electrostimulation system for delivering an electrostimulation treatment program to a patient with a reduced risk of inducing cardiac fibrillation, the electrostimulation system comprising:

an electrical pulse generator operable to generate electrical pulses according to an electrostimulation treatment program;

at least one electrode assembly electrically coupled to the pulse generator by at least one stimulation channel;

a command module coupled to the at least one stimulation channel and communicatively coupled to the pulse generator to control delivery of the electrostimulation treatment program to a patient via the electrode assembly; and a protection system microprocessor circuit communicatively coupled to the at least one stimulation channel and the command module and configured to:

monitor at least one current applied during the delivery of the electrostimulation treatment program;

apply a plurality of characteristic detection criteria to the monitored at least one current, the plurality of characteristic detection criteria identifying characteristics of an electrostimulation current that are indicative of a risk of inducing cardiac fibrillation when electrostimulation is applied to muscle groups proximate the cardiac region of the patient;

identify at least one characteristic of the monitored current that meets at least one of the characteristic detection criteria; and in response to identifying the at least one characteristic in the monitored current, alter an operating state of the electrostimulation system to reduce the risk of inducing cardiac fibrillation when electrostimulation is applied to muscle groups proximate the cardiac region of the patient.

2. The electrostimulation system of claim 1, wherein the electrostimulation system further comprises two stimulation channels, each stimulation channel comprising one electrode assembly of two electrodes, wherein each stimulation channel and electrode assembly is arranged in an H-bridge configuration.

3. The electrostimulation system of claim 2, wherein the identified at least one characteristic comprises a current present in more than one half of an H-bridge at a time, within a pulse.

4. The electrostimulation system of claim 1, wherein the identified at least one characteristic is selected from the group consisting of a pulse intensity above a preset limit; a pulse duration above a preset limit; an inappropriately compensated pulse; a charge per pulse above a predetermined limit; a current improperly exiting from a stimulation channel; a current present outside of a pulse; an excitation pulse and a compensation pulse generated on different channels; an inter-pulse time less than a predetermined limit; and a time between an excitation and a compensation pulse greater than a predetermined limit.

5. The electrostimulation system of claim 4, wherein the identified at least one characteristic is selected from the group consisting of a pulse intensity greater than about 152 milliamps; a pulse duration greater than about 1.5 milliseconds; a charge per pulse greater than about 10 micro-Coulombs; an inter-pulse time less than about 700 microseconds; and a time between excitation and compensation pulses greater than about one millisecond.

6. The electrostimulation system of claim 4, wherein an inappropriately compensated pulse is determined according to the relationship:

$$Q(t) = \int_0^t i(t')dt' \text{ with}(Q(0) = 0),$$

wherein Q is a pulse charge, t is a pulse duration, and i is a pulse intensity.

7. The electrostimulation system of claim 1, wherein the protection system comprises a microprocessor.

8. The electrostimulation system of claim 7, wherein the plurality of characteristics are at least partly programmable into the microprocessor.

9. The electrostimulation system of claim 8, wherein the microprocessor is electronically separate from the command module.

10. The electrostimulation system of claim 8, wherein at least one of the plurality of characteristics is based at least in part on patient-specific parameters.

11. The electrostimulation system of claim 7, wherein identifying at least one characteristic comprises iteratively comparing the at least one applied current to each of the plurality of characteristics.

12. A method of using an electrostimulation system including a protection system to reduce the risk of inducing cardiac fibrillation, the method comprising the steps of:

receiving a selection of an electrostimulation treatment program of the electrostimulation system;

generating electrostimulation pulses according to the selected program;

delivering the pulses to a patient via at least one electrode;

monitoring at least one current applied during the delivery of the electrostimulation treatment program;

applying a plurality of characteristic detection criteria to the monitored at least one current, the plurality of characteristic detection criteria identifying characteristics of an electrostimulation current that are indicative of a risk of inducing cardiac fibrillation when electrostimulation is applied to muscle groups proximate the cardiac region of the patient;

identifying, with the protection system, at least one characteristic of the monitored current that meets at least one of the characteristic detection criteria; and in response to identifying the at least one characteristic in the monitored current, altering an operating state of the electrostimulation system to reduce the risk of inducing cardiac fibrillation when electrostimulation is applied to muscle groups proximate the cardiac region of the patient.

13. The method of claim 12, wherein the step of identifying at least one characteristic further comprises identifying at least one characteristic selected from the group consisting of:

a pulse intensity above a preset limit;

a pulse duration above a preset limit;

an inappropriately compensated pulse;

a charge per pulse above a predetermined limit;

a current improperly exiting from a stimulation channel electrically coupled to the at least one electrode;

a current present in more than one half-bridge of the electrostimulation system at a time, within a pulse;

a current present outside of a pulse;

an excitation pulse and a compensation pulse generated on different channels of the electrostimulation system;

an inter-pulse time less than a predetermined limit; and a time between an excitation pulse and a compensation pulse greater than a predetermined limit.

14. The method of claim 13, wherein the step of identifying at least one characteristic further comprises identifying at least one characteristic selected from the group consisting of:

a pulse intensity greater than about 152 milliamps;

a pulse duration greater than about 1.5 milliseconds;

a charge per pulse greater than about 10 micro-Coulombs;

an inter-pulse time less than about 700 microseconds; and a time between excitation and compensation pulses greater than about one millisecond.

15. The method of claim 13, wherein the step of identifying at least one characteristic further comprises identifying an inappropriately compensated pulse according to the relationship:

$$Q(t) = \int_0^t i(t')dt' \text{ with}(Q(0) = 0),$$

wherein Q is a pulse charge, t is a pulse duration, and i is a pulse intensity.

16. The method of claim 13, wherein the step of altering an operating state of the electrostimulation system further comprises automatically powering off the electrostimulation system when the at least one characteristic is detected.

17. The method of claim 12, further comprising the steps of:
programming at least one electrostimulation treatment program; and
storing the at least one electrostimulation treatment program in the electrostimulation system.

18. An electrostimulation system including a protection system to reduce the risk of inducing cardiac fibrillation, the system comprising:
input means for selecting an electrostimulation treatment program of the electrostimulation system;
voltage generator means for generating electrostimulation pulses according to the selected program;
electrode means for delivering electrostimulation pulses according to the selected program to a patient; and
a protection system comprising microprocessor means for:
monitoring at least one current applied during the delivery of the electrostimulation treatment program;
applying a plurality of characteristic detection criteria to the monitored at least one current, the plurality of characteristic detection criteria identifying characteristics of an electrostimulation current that are indicative of a risk of inducing cardiac fibrillation when electrostimulation is applied to muscle groups proximate the cardiac region of the patient;
identifying at least one characteristic during application of the at least one of the monitored current that meets at least one of the characteristic detection criteria; and
in response to identifying the at least one characteristic in the monitored current, altering an operating state of the electrostimulation system to reduce the risk of inducing cardiac fibrillation when electrostimulation is applied to muscle groups proximate the cardiac region of the patient.

19. The electrostimulation system of claim 18, wherein the microprocessor means for identifying at least one characteristic further comprises means for identifying at least one characteristic selected from the group consisting of a pulse intensity above a preset limit; a pulse duration above a preset limit; an inappropriately compensated pulse; a charge per pulse above a predetermined limit; a current improperly exiting from a stimulation channel electrically coupled to the at least one electrode; a current present in more than one half-bridge of the electrostimulation system at a time, within a pulse; a current present outside of a pulse; an excitation pulse and a compensation pulse generated on different channels of the electrostimulation system; an inter-pulse time less than a predetermined limit; and a time between an excitation pulse and a compensation pulse greater than a predetermined limit.

20. The electrostimulation system of claim 19, wherein the microprocessor means for identifying at least one characteristic further comprises means for identifying at least one characteristic selected from the group consisting of a pulse intensity greater than about 152 milliamps; a pulse duration greater than about 1.5 milliseconds; a charge per pulse greater than about 10 micro-Coulombs; an inter-pulse time less than about 700 microseconds; and a time between excitation and compensation pulses greater than about one millisecond.

21. The electrostimulation system of claim 19, wherein the microprocessor means for identifying at least one characteristic further comprises means for identifying an inappropriately compensated pulse according to the relationship:

$$Q(t) = \int_0^t i(t')dt' \text{ with}(Q(0) = 0),$$

wherein Q is a pulse charge, t is a pulse duration, and i is a pulse intensity.

22. The electrostimulation system of claim 19, wherein the microprocessor means further comprises:
means for automatically powering off the electrostimulation system when the at least one characteristic is detected.

23. The electrostimulation system of claim 18, further comprising:
programming means for entering at least one electrostimulation treatment program; and
memory means for storing the at least one electrostimulation treatment program in the electrotherapy system.

24. A protection system for use with an electrostimulation system operable to deliver electrostimulation energy to a patient, the protection system comprising:
current monitoring circuitry configured to monitor current applied to the patient during electrostimulation;
characteristic detection circuitry configured to detect at least one characteristic of a monitored current that meets at least one of a plurality of characteristic detection criteria, such characteristics being indicative of a risk of inducing cardiac fibrillation when electrostimulation is applied to muscle groups proximate the cardiac region of the patient; and
a processor configured to alter the operating state of the electrostimulation system in response to the detection of the at least one characteristic in the monitored current to reduce the risk of inducing cardiac fibrillation when electrostimulation is applied to muscle groups proximate the cardiac region of the patient.

* * * * *